(12) United States Patent
Patel et al.

(10) Patent No.: US 9,610,277 B2
(45) Date of Patent: Apr. 4, 2017

(54) FORMULA COMPRISING A HYPOLIPIDEMIC AGENT

(71) Applicant: Cadila Healthcare Limited, Ahmedabad (IN)

(72) Inventors: Jitendre D. Patel, Ahmedabad (IN); Prakash Davadra, Ahmedabad (IN); Snehal Patel, Ahmedabad (IN); Shafiq Sheikh, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 14/899,912

(22) PCT Filed: Jul. 24, 2014

(86) PCT No.: PCT/IN2014/000489
§ 371 (c)(1),
(2) Date: Dec. 18, 2015

(87) PCT Pub. No.: WO2015/011730
PCT Pub. Date: Jan. 29, 2015

(65) Prior Publication Data
US 2016/0136131 A1    May 19, 2016

(30) Foreign Application Priority Data
Jul. 25, 2013   (IN) .................. 2470/MUM/2013

(51) Int. Cl.
*A61K 33/40*     (2006.01)
*A61K 31/40*     (2006.01)
*A61K 9/20*      (2006.01)

(52) U.S. Cl.
CPC ............ *A61K 31/40* (2013.01); *A61K 9/2009* (2013.01); *A61K 9/2013* (2013.01)

(58) Field of Classification Search
CPC ..... A61K 31/40; A61K 9/2009; A61K 9/2013
See application file for complete search history.

(56) References Cited

U.S. PATENT DOCUMENTS

2012/0121729 A1*   5/2012  Paterson ............... A61K 45/06
424/670

FOREIGN PATENT DOCUMENTS

WO   WO-2012104869 A1   8/2012
WO   WO-2014174524 A1   10/2014

OTHER PUBLICATIONS

Essentials of Pharmaceutical chemistry, Fourth Edition, 2012, p. 14).*

(Continued)

*Primary Examiner* — Savitha Rao
(74) *Attorney, Agent, or Firm* — Goodwin Procter LLP

(57) ABSTRACT

The present invention relates to the stable pharmaceutical composition of a suitable hypolipidemic agent. Preferably, the present invention discloses novel formulations of the compound of formula (I), or pharmaceutically acceptable salts of compounds of formula (I). More particularly the present invention relates to the stable pharmaceutical composition of compounds of formula (I) comprising compounds of formula (I) or its pharmaceutically acceptable salts, wherein the pH of the formulation is maintained above 7.

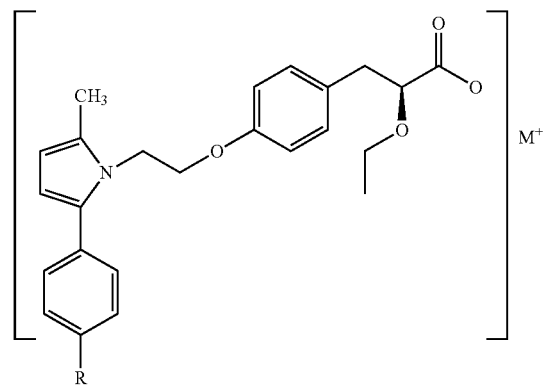

23 Claims, 1 Drawing Sheet

(56) References Cited

OTHER PUBLICATIONS

Ansel et al. (Pharmaceutical dosage forms and drug delivery systems, seventh edition 1999, p. 88-92.*
International Application No. PCT/IN2014/000489, International Search Report and Written Opinion mailed Nov. 20, 2014, 10 p.
International Application No. PCT/IN2014/000489, Response to Written Opinion filed May 21, 2015, 6 p.
International Application No. PCT/IN2014/000489, International Preliminary Report on Patentability mailed Oct. 9, 2015, 7 p.
"Sodium Stearyl Fumarate", obtained on Jun. 23, 2015. Retrieved from the Internet: <URL: https//www.medicinescomplete.com/me/excipients/current/ . . . >, 4 p.
Bharate, S.S., et al., "Interactions and Imcompatibilities of Pharmaceutical Excipients with Active Pharmaceutical Ingredients: A Comprehensive Review", J. Excipients and Food Chem., 1, (2010), 3-26.

\* cited by examiner

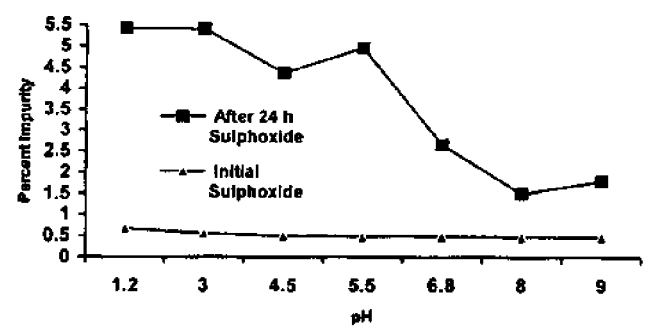

FORMULA COMPRISING A HYPOLIPIDEMIC AGENT

CLAIM OF PRIORITY

This application is a U.S. National Stage Filing under 35 U.S.C. 371 from International Application No. PCT/IN2014/000489, filed on Jul. 24, 2014, and published as WO 2015/011730 A1 on Jan. 29, 2015, which claims the benefit of priority under 35 U.S.C. §119 to Indian Provisional Patent Application No. 2470/MUM/2013, filed on Jul. 25, 2013, which are hereby incorporated by reference herein in their entireties.

FIELD OF THE INVENTION

The present invention relates to stable pharmaceutical compositions of a suitable hypolipidemic agent. Preferably, the present invention discloses novel formulations of the compound of formula (I), or pharmaceutically acceptable salts of compounds of formula (I). More particularly the present invention relates to the stable pharmaceutical composition of compounds of formula (I) comprising compounds of formula (I) or its pharmaceutically acceptable salts, wherein the pH of the formulation is maintained above 7.

BACKGROUND OF THE INVENTION

The compounds of formula (I) are new synthetic compounds having hypolipidemic activity. The compounds of formula (I) are used primarily for triglyceride lowering, with concomitant beneficial effect on glucose lowering and cholesterol lowering.

The structural formula of compounds of formula (I) is shown below.

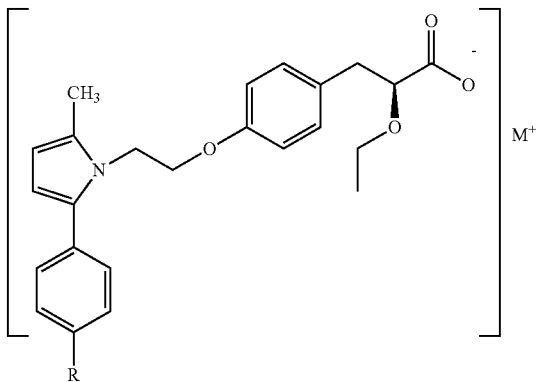

wherein 'R' is selected from hydroxy, hydroxyalkyl, acyl, alkoxy, alkylthio, thioalkyl, aryloxy, arylthio and $M^+$ represents suitable metal cations such as $Na^+$, $K^+$, $Ca^{+2}$, $Mg^{+2}$ and the like. Preferably, R is selected from alkylthio or thioalkyl groups; most preferably R represents —$SCH_3$. The $Mg^{+2}$ salt is preferred. The compounds of formula (I) are generally insoluble in water, but freely soluble in dimethyl sulfoxide, dichloromethane & slightly soluble in methanol and IPA.

The compounds of formula (I) are susceptible to oxidation, alkaline & acid hydrolysis and stress degradation during synthesis, purification and storage of the drug substance or when formulated as a dosage form. Sulfoxide and sulfone derivatives are the potential oxidized product.

The handling and storage particularly in the bulk form of pharmaceutically active ingredients which are sensitive to oxidation is difficult. Special handling is necessary and often the oxidation-sensitive ingredients are stored in airtight packaging under protective, gas. Substantial amounts of stabilizers are added during the formulating process of, such pharmaceutically active ingredients. In order to have a stable composition of compounds of formula (I), which meets the regulatory requirements, therefore, special packaging conditions will be required which is costly, difficult to manage and difficult to use in an industrial scale. Therefore, it is necessary to develop an alternate formulation which can stabilize the compound of formula (I) such that the expensive packaging requirements can be overcome.

WO 2012/104869 provides a therapeutic compound of formula (I) and their pharmaceutically acceptable salts for the prevention and treatment of lipodystrophy caused because of HIV infection or combination therapy of HIV-1 protease inhibitors (Pis) and/or reverse transcriptase inhibitors (nRTIs) by neutralizing lipohypertrophy, lipoatrophy and metabolic abnormalities in HIV patient. However, this document D1 does not disclose an alkalizing agent.

The inventors of the present invention surprisingly found that when suitable alkalinizer(s) are added into the formulation, the formulation remains stable. Further, one of the impurity (sulfoxide) which was being generated in API increases from 0.17% to 0.76% over a period of 6 months. Surprisingly, when suitable alkalinizer(s) are added which maintains the pH of the formulation above 7, the increase in the level of said impurity is restricted (from 0.13% to 0.26% over six months with no further increase with time). Therefore stabilization of compositions containing compounds of formula (I) can be made by maintaining the microenvironmental pH of composition above 7 by using suitable alkalinizers. Use of a suitable antioxidant(s) and chelating agent(s) further stabilizes the formulation.

SUMMARY OF THE INVENTION

The present invention, describes a stable pharmaceutical composition of compounds of formula (I) or their derivatives, wherein the microenvironmental pH of the composition is maintained above 7.

DESCRIPTION OF FIGURES

FIG. 1: Percentage of sulfoxide impurity level (0.3 RRT) at different pH after 24 hours.

FIG. 1 shows the percentage impurity level of sulfoxide. When the pH was modulated by addition of alkalinizer(s) then sulfoxide impurity level in API is restricted.

DETAILED DESCRIPTION OF THE INVENTION

The present invention describes a stable pharmaceutical composition of compounds of formula (I) or their derivatives,

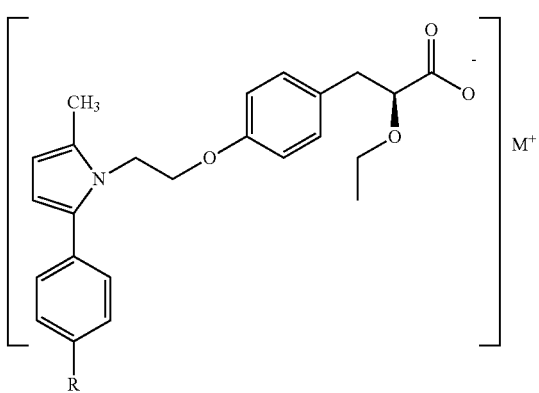

wherein 'R' is selected from hydroxy, hydroxyalkyl, acyl, alkoxy, alkylthio, thioalkyl, aryloxy, arylthio and M+ represents suitable metal cations such as Na+, K+, Ca2+, Mg+2 and the like and wherein the pH of the composition is maintained above 7.

In a preferred embodiment the compound of formula (I) represents Saroglitazar Magnesium of formula (Ia) having (Ia)

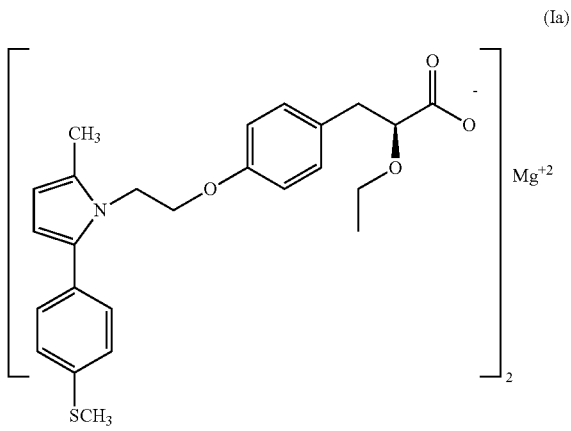

The present invention further describes a stable pharmaceutical composition of compounds of formula (I) or their derivatives, preferably a compound of formula (Ia), comprising one or more pharmaceutical excipients, alkainizers, antioxidants and chelating agents, wherein the pH of the composition is maintained above 7.

The pharmaceutical composition of compound of formula (I) or their derivatives of the present invention essentially comprises of
  suitable alkalinizers or suitable pH modifying agents which maintain the pH of the formulation above 7, and optionally
  a suitable stabilizer (antioxidants and chelating agents); and one or more other pharmaceutically acceptable excepients.

Suitable stabilizers may be selected from the classes of antioxidants or chelating agents. The other pharmaceutical excepients according to the present invention can be selected from suitable diluents, fillers, disintegrants, binder, lubricants, glidants, wetting agents, solvents and the like as is known in the art.

Antioxidants used according to the present invention include, but are not limited to citric acid, alpha tocopherol, sodium sulphite, sodium metabisulphite, butylated hydroxy anisole (BHA), BHT (2,6-di-tert-butyl-4-methylphenol), monothioglycerol, Vitamin C (ascorbic acid), and propyl gallate and combinations thereof and other similar material known to those of the ordinary skilled in the art.

Chelating agent used according to the present invention include, but are not limited to Disodium EDTA, citric acid and or its salts, maleic acid, chlorambutol, chlorhexidine or its salts, chlorocresol, combinations thereof and other similar material known to those of ordinary skill in the art.

Alkalinizers or suitable pH modifying agents which maintain the pH of the formulation above 7 used according to the present invention include, but are not limited to attapulgite, bentonite, calcium carbonate, calcium phosphate, calcium sulphate, mono ethanolamine, tri ethanolamine, potassium bicarbonate, potassium citrate, potassium hydroxide, sodium benzoate, sodium hydroxide, sodium sulfite, sodium bicarbonate, sodium carbonate, Disodium Hydrogen phosphate, mono basic potassium phosphate, Dicalcium phosphate, meglumine, light or heavy magnesium oxide and other similar excipients and their suitable combinations and other materials known to those of ordinary skill in the art.

As used herein, the term "binders" is intended to mean substances used to cause adhesion of powder particles in tablet granulations. Such compounds include, by way of example and without limitation, acacia alginic acid, tragacanth, carboxymethylcellulose sodium, poly(vinylpyrrolidone), compressible sugar (e.g., NuTab), ethyl cellulose, gelatin, liquid glucose, methyl cellulose, povidone and pregelatinized starch, combinations thereof and other similar materials known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC F68, PLURONIC F127), collagen, albumin, celluloses in non-aqueous solvents, and the like or their suitable combinations. Other binders which may be included may be, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "glidant" is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

As used herein, the term "lubricant" is intended to mean substances used in tablet formulations to reduce friction during tablet compression. Such compounds include, by way of example and without limitation, calcium stearate, magnesium stearate, mineral oil, stearic acid, zinc stearate, suitable combinations thereof and other such materials known to those of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pregelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

As used herein, the term "wetting agent" is intended to mean a compound used to aid in attaining intimate contact between solid particles and liquids. Exemplary wetting agents include, by way of example and without limitation, poloxamers, gelatin, casein, Glycerol mono-oleate, lecithin (phosphatides), gum acacia, cholesterol, tragacanth, stearic acid, benzalkonium chloride, calcium stearate, glycerol monostearate, cetostearyl alcohol, sodium lauryl sulphate, sodium dodecyl sulfate, salts of bile acids (taurocholate, glycocholate, cholate, deoxycholate, etc.), cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN), polyethylene glycols, polyoxyethylene stearates colloidal silicon dioxide, phosphates, sodium dodecylsulfate, carboxymethylcellulose calcium, carboxy methylcellulose sodium, methyl cellulose, hydroxyethylcellulose, hydroxylpropylcellulose, hydroxy propyl methyl cellulose phthalate, noncrystalline cellulose, magnesium aluminum silicate, triethanolamine, polyvinyl alcohol, and poly vinyl pyrrolidone (PVP) & their suitable combinations and other such materials known to those of ordinary skill in the art. Tyloxapol (a nonionic liquid polymer of the alkyl aryl polyether alcohol type, also known as superinone or triton) is another useful wetting agent which may be used.

The stable pharmaceutical composition according to the present invention may be in the form of a tablet or a caplet or a capsule or a powder or a suspension in a liquid or an aerosol formulation or solutions, preferably in the form of a tablet or capsule.

In another embodiment of the present invention, is described processes for the preparation of a stable pharmaceutical composition of compounds of formula (I), preferably a compound of formula (Ia), or their derivatives.

The stable pharmaceutical composition may be made by direct compression, wet granulation or dry granulation methods by techniques known to persons skilled in the art. Thus, for example, in the wet granulation process, the drug is mixed with one or more pharmaceutical excepients and granulated with suitable binding solution to form wet granules, the wet granules are dried and optionally sieved. The dried granules are mixed with one or more suitable excepients from those described elsewhere and then compressed into tablets or filled into capsules.

In direct compression process, the drug is mixed with all the pharmaceutical excepients required and then is either compressed into tablets or filled in capsules.

In dry granulation process, the drug is mixed with one or more pharmaceutical excepients and compressed into slugs and these slugs are passed through required sieve.

The sieved granules are mixed with one or more suitable excepients from those described elsewhere and then compressed into tablets or filled into capsules.

One or more solvents used in the formulation are selected from acetone, chloroform, dichloromethane, ethyl alcohol, ethyl acetate, methyl alcohol, isopropyl alcohol and combinations thereof and other such materials known to those of ordinary skill in the art.

About 1% w/v aqueous dispersion of tablets was used for pH measurement. pH degradation can be seen with API when kept in different standard pH buffers. Percentage individual impurity at 0.3 RRT (Sulphoxide impurity) decreases as the solution of pH increases above pH 7 as shown in FIG. 1.

The invention as described earlier is further demonstrated in illustrative examples 1 to 9 below. These examples are provided as illustration only and therefore should not be considered as a limitation of the scope of the invention.

The following formulations were prepared using different chelating agents, alkalinizers and anti-oxidants by dry granulation techniques:

Brief Manufacturing Procedure:

1.0. Granulation
i) Intragranular excipients and API [compound of formula (IA)] are weighed accurately and mixed properly.
ii) To the dry blend IPA is added and the blend is granulated.
iii) Wet mass is passed through #10 and the wet granules are dried in FBD at a temperature below 60° C.

Extragranular Addition
Colloidal silicon is weighed and passed along with the dried granules through-#30. The colloidal silicon is mixed with the granules in the conta blender and to the dried mass Talc and Magnesium stereate is added and mixed.

2.0. Direct Compression
All intragranular excipients and API are weighed accurately and mixed properly and blended in the conta blender. Extragranular excipients were added and lubricated in conta blender. The granules or blend is compressed into tablets or filled into capsules.

3.0 Dry Granulation
All excipients are mixed and passed through a roller compactor. Obtained pellets are then subjected to milling to get uniform powder which is the lubricated and followed by compression.

TABLE 1

| Test | Percent Purity at 40° C./75% RH | | | |
|---|---|---|---|---|
|  | Initial | 1 Month | 2 Month | 3 Month |
| Purity | 98.48 | 98.10 | 97.93 | 97.17 |
| Water By KF | 0.62 | 1.17 | 2.32 | 2.57 |

Table 1 shows that moisture absorption of API increases when exposed to 40° C./75% RH condition. Therefore the inventors of the present invention have tried to develop a stable formulation of API such that the API is protected and cannot absorb moisture.

Initial formulations without alkalinizers were prepared as provided in Table 2 and were tested for their stability by loading them in stability chambers as per techniques and protocols known in the art as shown in Table 2. Table 3 provides the stability data of these formulations.

TABLE 2

| Ingredient | % w/w | | |
|---|---|---|---|
|  | Ex 1 | Ex 2 | Ex 3 |
| Compound (Ia) | 1.00 | 1.54 | 1.54 |
| Disodium EDTA | 2.00 | — | — |

TABLE 2-continued

| | % w/w | | |
|---|---|---|---|
| Ingredient | Ex 1 | Ex 2 | Ex 3 |
| Disodium hydrogen phosphate | — | — | — |
| Light magnesium oxide | — | — | — |
| Meglumin | — | — | — |
| Sodium Bicarbonate | — | — | — |
| Sodium metabisulfite | — | 1.00 | 0.50 |
| Propyl Gallate | — | — | — |
| Alpha Tocopherol | 8.00 | — | — |
| Lactose Anhydrous | — | 86.81 | 87.31 |
| Microcrystalline cellulose | — | — | — |
| Dibasic Calcium Phosphate | 65.50 | — | — |
| Acdisol | 14.00 | 4.15 | 4.15 |
| Povidone K-30 | 6.00 | 5.00 | 5.00 |
| Purified water | — | — | — |
| Puririfed Talc | 1.00 | 0.50 | 0.50 |
| Aerosil | 1.50 | 0.50 | 0.50 |
| Magnesium Stearate | 1.00 | 0.50 | 0.50 |

TABLE 3

One month stability data of the formulations of Table 2

| | Percent Purity at 40° C./75% RH | |
|---|---|---|
| Batch No. | Initial | 1 Month |
| Ex 1 | 97.89 | 91.57 |
| Ex 2 | 98.58 | 96.88 |
| Ex 3 | 98.59 | 97.39 |

It can be seen that from Table 3 that these formulations which do not contain any alkalinizers have poor stability.

Subsequently, alkalinizers were added and table 4 shows such alkalizer containing formulations. These formulations were also tested for their stability by loading them in stability chambers as per techniques and protocols known in the art as shown in Table 5.

TABLE 4

| Ingredient | Ex 4 | Ex 5 | Ex 6 | Ex 7 | Ex 8 | Ex 9 |
|---|---|---|---|---|---|---|
| Compound (1a) | 3.08 | 1.54 | 1.54 | 1.54 | 1.54 | 1.54 |
| Disodium EDTA | — | — | — | — | — | 2.00 |
| Disodium hydrogen phosphate | — | — | 1.00 | 1.00 | 1.00 | 1.00 |
| Light magnesium oxide | 6.15 | — | — | — | — | — |
| Meglumin | — | — | — | — | — | — |
| Sodium Bicarbonate | — | 9.00 | — | — | — | — |
| Sodium metabisulfite | — | — | 1.00 | — | — | — |
| Propyl Gallate | — | — | — | 0.10 | — | — |
| Alpha Tocopherol | — | — | — | — | 8.00 | — |
| Lactose Anhydrous | 23.07 | 78.81 | 85.81 | 86.71 | 78.81 | 84.81 |
| Microcrystalline cellulose | 50.00 | — | — | — | — | — |
| Dibasic Calcium Phosphate | — | — | — | — | — | — |
| Acdisol | 9.23 | 4.15 | 4.15 | 4.15 | 4.15 | 4.15 |
| Povidone K-30 | 3.85 | 5.00 | 5.00 | 5.00 | 5.00 | 5.00 |
| Purified water | — | — | — | — | — | — |
| Puririfed Talc | 1.54 | 0.50 | 0.50 | 0.50 | 0.50 | 0.50 |
| Aerosil | 1.54 | 0.50 | 0.50 | 0.50 | 0.50 | 0.50 |

TABLE 4-continued

| Ingredient | Ex 4 | Ex 5 | Ex 6 | Ex 7 | Ex 8 | Ex 9 |
|---|---|---|---|---|---|---|
| Magnesium Stearate | 1.54 | 0.50 | 0.50 | 0.50 | 0.50 | 0.50 |

TABLE 5

Three months stability data of the formulations of Table 4

| Ex No | Initial | 1 Month | 2 Month | 3 Month |
|---|---|---|---|---|
| Ex 4 | 99.10 | 98.60 | 98.50 | 98.30 |
| Ex 5 | 98.40 | 98.03 | 97.66 | 97.53 |
| Ex 6 | 98.43 | 98.17 | 97.5 | 97.45 |
| Ex 7 | 98.36 | 97.82 | 97.6 | 97.44 |
| Ex 8 | 98.46 | 98.06 | 97.83 | 97.42 |
| Ex 9 | 98.34 | 97.78 | 97.52 | 97.42 |

The formulations containing alkalinizer are stable as can be seen from the above table 5.

The above stability data shows that the formulations are stable and the compound of formula (I) is effectively stabilized by addition of suitable alkalinizers so that it may be used in clinical trials and subsequently as a commercial product.

We claim:

1. A stable pharmaceutical composition comprising a compound of formula (I):

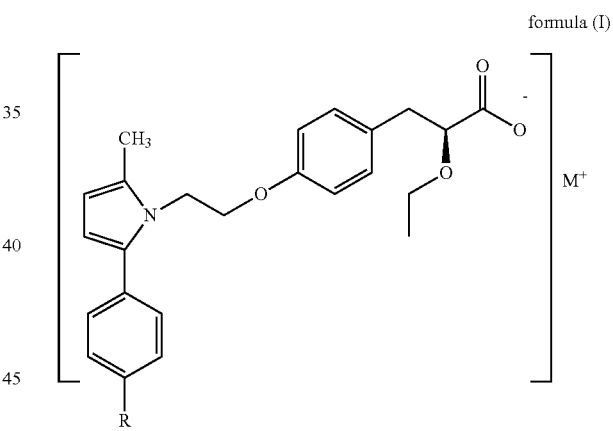

formula (I)

wherein
R is alkylthio or thioalkyl;
$M^+$ represents a metal cation;
the pH of the composition is above 7; and
the composition comprises
  i) suitable alkalinizers or suitable pH modifying agents which maintain the pH of the formulation above 7, and optionally
  ii) a suitable stabilizer; and
  iii) one or more other pharmaceutically acceptable excipients.

2. The pharmaceutical composition as claimed in claim 1 wherein R is selected from alkylthio or thioalkyl and $M^+$ represents $Mg^{+2}$.

3. The pharmaceutical composition as claimed in claim 1 wherein R is $SCH_3$.

4. The pharmaceutical composition as claimed in claim 1 wherein the alkalinizers or pH modifying agents is selected from attapulgite, bentonite, calcium carbonate, calcium phosphate, calcium sulphate, mono ethanolamine, tri ethanolamine, potassium bicarbonate, potassium citrate, potassium hydroxide, sodium bicarbonate, Disodium hydrogen phosphate, mono basic potassium phosphate, Dicalcium phosphate, meglumine, light or heavy magnesium oxide.

5. The pharmaceutical composition as claimed in claim 4 wherein the alkalinizers or pH modifying agents is Disodium hydrogen phosphate or magnesium oxide.

6. The pharmaceutical composition as claimed in claim 1 wherein the stabilizers are selected from the classes of suitable antioxidants or chelating agents.

7. The pharmaceutical composition as claimed in claim 6, wherein the antioxidants are selected from citric acid, alpha tocopherol, sodium sulphite, sodium metabisulphite, butylated hydroxy anisole (BHA), BHT (2,6-di-tert-butyl-4-methylphenol), monothioglycerol, Vitamin C (ascorbic acid), propyl gallate or suitable combinations thereof.

8. The pharmaceutical composition as claimed in claim 6 wherein the chelating agent is selected from Disodium EDTA, citric acid or its salts, maleic acid, chlorambutol, chlorhexidine or its salts, chlorocresol or their suitable combinations.

9. The pharmaceutical composition as claimed in claim 1 wherein the other pharmaceutical excipients are selected from suitable diluents, fillers, disintegrants, binder, lubricants, glidants, wetting agents and solvent(s).

10. The pharmaceutical composition as claimed in claim 9 wherein the binder is selected from acacia alginic acid, tragacanth, carboxymethylcellulose sodium, poly (vinylpyrrolidone), compressible sugar, ethyl cellulose, gelatin, liquid glucose, methyl cellulose, povidone and pregelatinized starch or suitable combinations thereof.

11. The pharmaceutical composition as claimed in claim 9 wherein the diluent or filler is selected from dibasic calcium phosphate, kaolin, sucrose, mannitol, microcrystalline cellulose, powdered cellulose, precipitated calcium carbonate, sorbitol, starch or suitable combinations thereof.

12. The pharmaceutical composition as claimed in claim 9 wherein the lubricant is selected from calcium stearate, magnesium stearate, mineral oil, stearic acid, zinc stearate or suitable combinations thereof.

13. The pharmaceutical composition as claimed in claim 9 wherein the disintegrant is selected from corn starch, potato starch, pregelatinized and modified starched thereof, sweeteners, clays, microcrystalline cellulose, carsium, alginates, sodium starch glycolate, gums selected from agar, guar, locust bean, karaya, pectin, tragacanth or combinations thereof.

14. The pharmaceutical composition as claimed in claim 9 wherein glidants is selected from colloidal silica, calcium silicate, magnesium silicate, silicon hydrogel, cornstarch, talc or suitable combinations thereof.

15. The pharmaceutical composition as claimed in claim 1 wherein the pharmaceutical composition is in the form of a tablet or a caplet or a capsule or a powder or a suspension in a liquid or an aerosol formulation or solutions.

16. The pharmaceutical composition as claimed in claim 1 prepared by direct compression, wet granulation or dry granulation.

17. The pharmaceutical composition as claimed in claim 16 wherein the composition is prepared by direct compression comprising mixing the drug with all the pharmaceutical excipients required and then either compressing into tablets or filled in capsules.

18. The pharmaceutical composition as claimed in claim 3 wherein $M^+$ represents $Na^+$ or $K^+$.

19. The pharmaceutical composition as claimed in claim 3 wherein $M^+$ represents $Ca^{+2}$ or $Mg^{+2}$.

20. The pharmaceutical composition as claimed in claim 1 wherein the compound of formula (I) is the compound of formula (Ia):

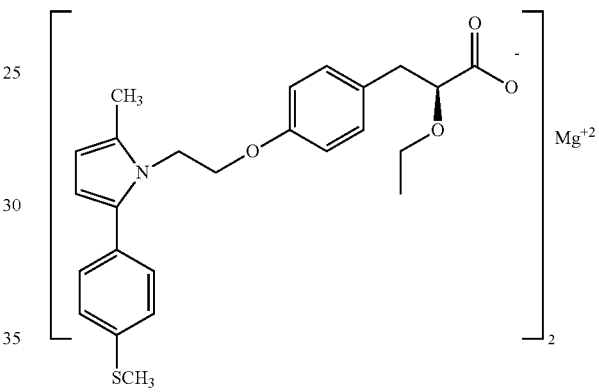

(Ia)

21. The pharmaceutical composition as claimed in claim 1 wherein the alkalinizer or pH modifying agent is selected from the group consisting of potassium bicarbonate, potassium citrate, sodium bicarbonate, disodium hydrogen phosphate, and monobasic potassium phosphate.

22. The pharmaceutical composition as claimed in claim 20 wherein the alkalinizer or pH modifying agent is selected from the group consisting of potassium bicarbonate, potassium citrate, sodium bicarbonate, disodium hydrogen phosphate, and monobasic potassium phosphate.

23. The pharmaceutical composition as claimed in claim 20 wherein the alkalinizer or pH modifying agent is disodium hydrogen phosphate or magnesium oxide.

* * * * *